United States Patent [19]

Gallenkamp et al.

[11] Patent Number: 5,783,734
[45] Date of Patent: Jul. 21, 1998

[54] PROCESS FOR PREPARING N-METHYL-N'-NITROGUANIDINE

[75] Inventors: Bernd Gallenkamp; Lothar Rohe, both of Wuppertal, Germany

[73] Assignee: Bayer Aktiengesellschaft, Leverkusen, Germany

[21] Appl. No.: 820,274

[22] Filed: Mar. 18, 1997

[30] Foreign Application Priority Data

Mar. 25, 1996 [DE] Germany ............... 196 11 654.6

[51] Int. Cl.⁶ ............................................. C07C 277/08
[52] U.S. Cl. ............................................. 564/108
[58] Field of Search ............................................. 564/108

[56] References Cited

U.S. PATENT DOCUMENTS 2,559,085  7/1951  McKay et al. ............... 260/565

OTHER PUBLICATIONS

McKay et al. "Preparation and Properties of N–Methyl–N–nitroso–N'–nitroguanidine," J. Am. Chem. Soc., vol. 69, pp. 3028–3030, Dec. 1947.

Journal of the American Chemical Society, Bd. 69, 1947, pp. 3028–3030, A.F. McKay et al., "Preparation and properties of N–methyl–N–nitroso–N'–ntroguanidine".

Primary Examiner—Peter O'Sullivan
Attorney, Agent, or Firm—Sprung Kramer Schaefer & Briscoe

[57] ABSTRACT

The present invention relates to a novel process for preparing N-methyl-N'-nitroguanidine by reacting nitroguanidine with aqueous methylamine solution at 0° to 40° C.

1 Claim, No Drawings

PROCESS FOR PREPARING N-METHYL-N'-NITROGUANIDINE

The invention relates to a novel process for preparing N-methyl-N'-nitroguanidine.

It is known that N-methyl-N'-nitroguanidine is obtained on initially nitration of S-methylisothiuronium sulfate of the formula (A) in a conventional manner and subsequently, in a second reaction step, replacing the mercapto group with methylamine according to the following reaction scheme:

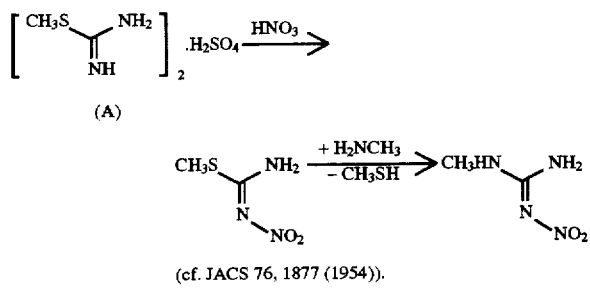

(cf. JACS 76, 1877 (1954)).

However, this process has the disadvantage of being a two-step reaction. Although the yields in both steps are relatively good, technical problems are caused by the elimination of methyl mercaptan, especially in a preparation on an industrial scale.

It is further known that N-methyl-N'-nitroguanidine can be obtained by reacting an alkaline solution (potassium hydroxide) of nitroguanidine with methylamine hydrochloride at 60° C. according to the following reaction scheme:

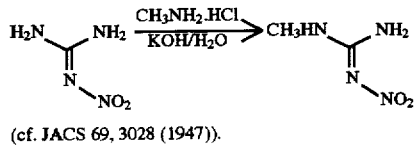

(cf. JACS 69, 3028 (1947)).

However, this process has the disadvantage that to obtain a pure product at least one to two recrystallizations are necessary to remove inorganic impurities, leading to a noticeable reduction in yield.

It has now been found that N-methyl-N'-nitroguanidine of the formula (I)

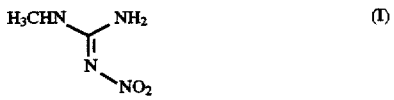

is obtained when nitroguanidine of the formula (II)

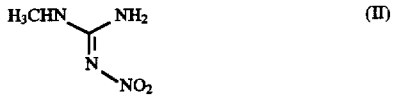

is reacted with aqueous methylamine solution at temperatures between 0° C. and 40° C.

Surprisingly, N-methyl-N'-nitroguanidine of the formula (I) can be obtained in a simple manner in very good yields and high purity by the process according to the invention, although there was nothing in the prior art to suggest that the reaction would be so successful under these mild conditions. Furthermore, the high selectivity of the reaction according to the invention is surprising; dialkylation is not observed.

The reaction according to the invention therefore has the advantage of better industrial practicability while simultaneously giving high yields. Specific benefits are: auxiliaries are not necessary, low reaction temperature, simple isolation of the final product without separate purification steps and avoiding methyl mercaptan.

The reaction according to the process of the invention may be outlined by the following reaction scheme:

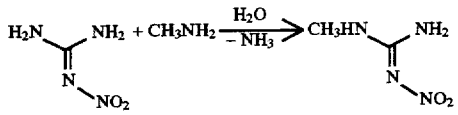

The starting materials, nitroguanidine of the formula (II) and methylamine, are commonly known compounds of organic chemistry.

The process according to the invention is conducted in the presence of water as diluent. However it is also possible to work in organic/aqueous systems, in which case all the customary water-miscible organic solvents can be used. Examples are ketones, such as acetone, methyl ethyl ketone or methyl isobutyl ketone; nitriles, such as acetonitrile or propionitrile, and also alcohols, such as methanol or ethanol.

When conducting the process according to the invention, reaction temperatures can be varied over a relatively wide range. Generally, the reaction is carried out at temperatures between 10° C. and 30° C., preferably at room temperature.

When conducting the process according to the invention, generally 1 to 3 mol, preferably 1 to 2 mol, of methylamine are used per mole of nitroguanidine of the formula (II).

In a special embodiment of the process according to the invention both the starting materials are used directly as aqueous solutions.

Workup is done in the usual manner.

The N-Methyl-N'-nitroguanidine of the formula (I) to be prepared by the process according to the invention can be used as an intermediate in the preparation of biologically active compounds, for example insecticides (cf. for example EP-A 0 376 279 and EP-A 0 428 941).

PREPARATION EXAMPLES

Example 1

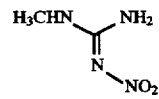

At 18° to 20° C., 150 g (about 1.5 mol) of about 30% strength aqueous methylamine solution are added dropwise to a suspension of 138.8 g (1 mol) of nitroguanidine (containing about 25% water) in 750 ml of water over 10 minutes. The reaction mixture is subsequently stirred at 20° to 25° C. for 24 hours. Thereafter the temperature is lowered to about 5° C., the precipitate is removed by filtration under suction, washed with mother liquor, sucked dry, washed once more with petroleum ether, and dried in a vacuum oven at 45° C.

100.8 g (85.4% of theory) of N-methyl-N'-nitroguanidine of melting point of 159° C. with a grade of purity of 100% (by HPLC) are obtained.

We claim:
1. A process for preparating N-methyl-N'-nitroguanidine of the formula (I)
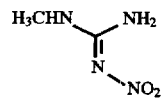 (I)
characterized in that nitroguanidine of the formula (II)
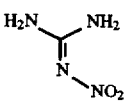 (II)
is reacted with aqueous methylamine solution at temperatures between 0° C. and 40° C.
* * * * *